(12) United States Patent
Chambers et al.

(10) Patent No.: US 11,957,577 B2
(45) Date of Patent: Apr. 16, 2024

(54) SYSTEMS, METHODS AND DEVICES FOR DELIVERY SYSTEMS, METHODS AND DEVICES FOR IMPLANTING PROSTHETIC HEART VALVES

(71) Applicant: 4C Medical Technologies, Inc., Maple Grove, MN (US)

(72) Inventors: Jeffrey W. Chambers, Maple Grove, MN (US); Gregory G. Brucker, Maple Grove, MN (US); Joseph P. Higgins, Minnetonka, MN (US); Saravana B. Kumar, Minnetonka, MN (US); Jason S. Diedering, Minneapolis, MN (US); Karl A. Kabarowski, Maple Grove, MN (US); Robert J. Thatcher, Blaine, MN (US); James E. Flaherty, Maple Grove, MN (US); Jeffrey R. Stone, Minnetonka, MN (US)

(73) Assignee: 4C Medical Technologies, Inc., Maple Grove, MN (US)

(*) Notice: Subject to any disclaimer, the term of this patent is extended or adjusted under 35 U.S.C. 154(b) by 478 days.

(21) Appl. No.: 16/835,474

(22) Filed: Mar. 31, 2020

(65) Prior Publication Data

US 2020/0222179 A1  Jul. 16, 2020

Related U.S. Application Data

(63) Continuation of application No. 15/874,376, filed on Jan. 18, 2018, now Pat. No. 10,653,523.
(Continued)

(51) Int. Cl.
*A61F 2/24* (2006.01)

(52) U.S. Cl.
CPC ............ *A61F 2/243* (2013.01); *A61F 2/2418* (2013.01); *A61F 2/2436* (2013.01); *A61F 2/2439* (2013.01)

(58) Field of Classification Search
CPC ...... A61F 2/2427; A61F 2/243; A61F 2/2436; A61F 2/2439; A61M 25/0147
See application file for complete search history.

(56) References Cited

U.S. PATENT DOCUMENTS

| 4,424,833 A | 1/1984 | Spector |
| 4,503,569 A | 3/1985 | Dotter |

(Continued)

FOREIGN PATENT DOCUMENTS

| AU | 2014203064 B2 | 6/2015 |
| AU | 2015230879 A1 | 10/2015 |

(Continued)

OTHER PUBLICATIONS

International Search Report and Written Opinion, dated May 15, 2018, in PCT Application No. PCT/US18/14400, filed Jan. 19, 2018.

(Continued)

*Primary Examiner* — Diane D Yabut
(74) *Attorney, Agent, or Firm* — Weiss & Arons LLP

(57) ABSTRACT

Embodiments of delivery systems, devices and methods for delivering a prosthetic heart valve device to a heart chamber for expanded implementation are disclosed. More specifically, methods, systems and devices are disclosed for delivering a self-expanding prosthetic mitral valve device to the left atrium, with no engagement of the left ventricle, the native mitral valve leaflets or the annular tissue downstream of the upper annular surface during delivery, and in some embodiments with no engagement of the ventricle, mitral valve leaflets and/or annular tissue located downstream of (Continued)

the upper annular surface by the delivered, positioned and expanded prosthetic mitral valve device.

25 Claims, 10 Drawing Sheets

Related U.S. Application Data

(60) Provisional application No. 62/448,036, filed on Jan. 19, 2017.

(56) References Cited

U.S. PATENT DOCUMENTS

| | | |
|---|---|---|
| 4,733,665 A | 3/1988 | Palmaz |
| 4,878,906 A | 11/1989 | Lindemann |
| 5,190,528 A | 3/1993 | Fonger |
| 5,415,667 A | 5/1995 | Frater |
| 5,441,483 A | 8/1995 | Avitall |
| 5,693,083 A | 12/1997 | Baker |
| 5,693,089 A | 12/1997 | Inoue |
| 5,776,188 A | 7/1998 | Shepherd |
| 5,843,090 A | 12/1998 | Schuetz |
| 5,928,258 A | 7/1999 | Khan |
| 5,957,949 A | 9/1999 | Leonhardt |
| 5,968,070 A | 10/1999 | Bley |
| 6,123,723 A | 9/2000 | Konya |
| 6,152,144 A | 11/2000 | Lesh |
| 6,231,602 B1 | 5/2001 | Carpentier |
| 6,287,334 B1 | 9/2001 | Moll |
| 6,319,280 B1 | 11/2001 | Schoon |
| 6,319,281 B1 | 11/2001 | Patel |
| 6,332,893 B1 | 12/2001 | Mortier |
| 6,371,983 B1 | 4/2002 | Lane |
| 6,409,758 B2 | 6/2002 | Stobie |
| 6,425,916 B1 | 7/2002 | Garrison |
| 6,471,718 B1 | 10/2002 | Staehle |
| 6,494,909 B2 | 12/2002 | Greenhalgh |
| 6,503,272 B2 | 1/2003 | Duerig |
| 6,540,782 B1 | 4/2003 | Snyders |
| 6,569,196 B1 | 5/2003 | Vesely |
| 6,589,275 B1 | 7/2003 | Ivancev |
| 6,702,826 B2 | 3/2004 | Liddicoat |
| 6,738,655 B1 | 5/2004 | Sen |
| 6,790,231 B2 | 9/2004 | Liddicoat |
| 6,790,237 B2 | 9/2004 | Stinson |
| 6,821,297 B2 | 11/2004 | Snyders |
| 6,830,585 B1 | 12/2004 | Artof |
| 6,840,957 B2 | 1/2005 | Dimatteo |
| 6,875,231 B2 | 4/2005 | Anduiza |
| 7,011,671 B2 | 3/2006 | Welch |
| 7,041,132 B2 | 5/2006 | Quijano |
| 7,044,966 B2 | 5/2006 | Svanidze |
| 7,125,420 B2 | 10/2006 | Rourke |
| 7,153,324 B2 | 12/2006 | Case |
| 7,252,682 B2 | 8/2007 | Seguin |
| 7,276,077 B2 | 10/2007 | Zadno-Azizi |
| 7,276,078 B2 | 10/2007 | Spenser |
| 7,291,168 B2 | 11/2007 | Macoviak |
| 7,364,588 B2 | 4/2008 | Mathis |
| 7,381,220 B2 | 6/2008 | Macoviak |
| 7,442,204 B2 | 10/2008 | Schwammenthal |
| 7,445,631 B2 | 11/2008 | Salahieh |
| 7,455,689 B2 | 11/2008 | Johnson |
| 7,510,572 B2 | 3/2009 | Gabbay |
| 7,524,331 B2 | 4/2009 | Birdsall |
| 7,704,277 B2 | 4/2010 | Zakay |
| 7,749,266 B2 | 7/2010 | Forster |
| 7,758,491 B2 | 7/2010 | Buckner |
| 7,780,723 B2 | 8/2010 | Taylor |
| 7,789,909 B2 | 9/2010 | Andersen |
| 7,935,144 B2 | 5/2011 | Robin |
| 7,959,672 B2 | 6/2011 | Salahieh |
| 7,967,853 B2 | 6/2011 | Eidenschink |
| 7,998,196 B2 | 8/2011 | Mathison |
| 8,012,201 B2 | 9/2011 | Lashinski |
| 8,016,877 B2 | 9/2011 | Seguin |
| 8,021,420 B2 | 9/2011 | Dolan |
| 8,029,556 B2 | 10/2011 | Rowe |
| D648,854 S | 11/2011 | Braido |
| 8,052,592 B2 | 11/2011 | Goldfarb |
| 8,057,493 B2 | 11/2011 | Goldfarb |
| 8,070,802 B2 | 12/2011 | Lamphere |
| 8,083,793 B2 | 12/2011 | Lane |
| D653,341 S | 1/2012 | Braido |
| D653,342 S | 1/2012 | Braido |
| 8,092,524 B2 | 1/2012 | Nugent |
| 8,142,492 B2 | 3/2012 | Forster |
| 8,147,541 B2 | 4/2012 | Forster |
| D660,433 S | 5/2012 | Braido |
| D660,967 S | 5/2012 | Braido |
| 8,167,932 B2 | 5/2012 | Bourang |
| 8,236,049 B2 | 8/2012 | Rowe |
| 8,246,677 B2 | 8/2012 | Ryan |
| 8,287,538 B2 | 10/2012 | Brenzel et al. |
| 8,308,798 B2 | 11/2012 | Pintor |
| 8,348,998 B2 | 1/2013 | Pintor |
| 8,348,999 B2 | 1/2013 | Kheradvar |
| 8,366,768 B2 | 2/2013 | Zhang |
| 8,398,708 B2 | 3/2013 | Meiri |
| 8,409,275 B2 | 4/2013 | Matheny |
| 8,414,644 B2 | 4/2013 | Quadri |
| 8,414,645 B2 | 4/2013 | Dwork |
| 8,439,970 B2 | 5/2013 | Jimenez |
| 8,454,686 B2 | 6/2013 | Alkhatib |
| 8,465,541 B2 | 6/2013 | Dwork |
| 8,491,650 B2 | 7/2013 | Wiemeyer |
| 8,512,400 B2 | 8/2013 | Tran |
| 8,518,106 B2 | 8/2013 | Duffy |
| 8,535,373 B2 | 9/2013 | Stacchino |
| 8,562,673 B2 | 10/2013 | Yeung |
| 8,568,472 B2 | 10/2013 | Marchand |
| 8,579,963 B2 | 11/2013 | Tabor |
| 8,579,964 B2 | 11/2013 | Lane |
| 8,603,159 B2 | 12/2013 | Seguin |
| 8,623,075 B2 | 1/2014 | Murray, III |
| 8,636,764 B2 | 1/2014 | Miles |
| 8,641,757 B2 | 2/2014 | Pintor |
| 8,657,870 B2 | 2/2014 | Turovskiy |
| 8,663,318 B2 | 3/2014 | Ho |
| 8,679,176 B2 | 3/2014 | Matheny |
| 8,721,715 B2 | 5/2014 | Wang |
| 8,740,976 B2 | 6/2014 | Tran |
| 8,747,459 B2 | 6/2014 | Nguyen |
| 8,747,461 B2 | 6/2014 | Centola |
| 8,764,793 B2 | 7/2014 | Lee |
| 8,764,820 B2 | 7/2014 | Dehdashtian |
| 8,778,020 B2 | 7/2014 | Gregg |
| 8,790,396 B2 | 7/2014 | Bergheim |
| 8,795,354 B2 | 8/2014 | Benichou |
| 8,795,357 B2 | 8/2014 | Yohanan |
| 8,805,466 B2 | 8/2014 | Salahieh |
| 8,814,931 B2 | 8/2014 | Wang |
| 8,828,043 B2 | 9/2014 | Chambers |
| 8,828,051 B2 | 9/2014 | Javois |
| 8,845,711 B2 | 9/2014 | Miles |
| 8,845,722 B2 | 9/2014 | Gabbay |
| 8,852,271 B2 | 10/2014 | Murray, III |
| 8,852,272 B2 | 10/2014 | Gross |
| 8,870,949 B2 | 10/2014 | Rowe |
| 8,876,897 B2 | 11/2014 | Kheradvar |
| 8,906,022 B2 | 12/2014 | Krinke et al. |
| 8,926,692 B2 | 1/2015 | Dwork |
| 8,956,402 B2 | 2/2015 | Cohn |
| 8,956,405 B2 | 2/2015 | Wang |
| 8,961,518 B2 | 2/2015 | Kyle et al. |
| 8,986,372 B2 | 3/2015 | Murry, III |
| 8,986,374 B2 | 3/2015 | Cao |
| 8,986,375 B2 | 3/2015 | Garde |
| 8,998,980 B2 | 4/2015 | Shipley |
| 8,998,982 B2 | 4/2015 | Richter |
| 9,005,273 B2 | 4/2015 | Salahieh |
| 9,011,527 B2 | 4/2015 | Li |
| D730,520 S | 5/2015 | Braido |

(56) References Cited

U.S. PATENT DOCUMENTS

| | | |
|---|---|---|
| D730,521 S | 5/2015 | Braido |
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |
| 9,138,313 B2 | 9/2015 | McGuckin, Jr. |
| 9,144,493 B2 | 9/2015 | Carr |
| 9,144,494 B2 | 9/2015 | Murray |
| 9,155,619 B2 | 10/2015 | Liu |
| 9,161,835 B2 | 10/2015 | Rankin |
| 9,173,737 B2 | 11/2015 | Hill |
| 9,192,466 B2 | 11/2015 | Kovalsky |
| 9,226,820 B2 | 1/2016 | Braido |
| 9,232,942 B2 | 1/2016 | Seguin |
| 9,232,996 B2 | 1/2016 | Sun |
| 9,248,016 B2 | 2/2016 | Oba |
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr |
| 9,439,763 B2 | 9/2016 | Geist |
| 9,439,795 B2 | 9/2016 | Wang |
| 9,480,560 B2 | 11/2016 | Quadri |
| 9,498,370 B2 | 11/2016 | Kyle et al. |
| 9,504,569 B2 | 11/2016 | Malewicz |
| 9,522,062 B2 | 12/2016 | Tuval |
| 9,566,152 B2 | 2/2017 | Schweich, Jr |
| 9,579,194 B2 | 2/2017 | Elizondo |
| 9,579,197 B2 | 2/2017 | Duffy |
| 9,622,863 B2 | 4/2017 | Karapetian |
| 9,717,592 B2 | 8/2017 | Thapliyal |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola et al. |
| 9,839,765 B2 | 12/2017 | Morris |
| 9,861,477 B2 | 1/2018 | Backus |
| 9,872,765 B2 | 1/2018 | Zeng |
| 9,877,830 B2 | 1/2018 | Lim |
| 9,968,443 B2 | 5/2018 | Bruchman |
| 10,004,601 B2 | 6/2018 | Tuval |
| 10,016,274 B2 | 7/2018 | Tabor |
| 10,016,275 B2 | 7/2018 | Nyuli |
| 10,022,132 B2 | 7/2018 | Wlodarski et al. |
| 10,034,750 B2 | 7/2018 | Morriss |
| 10,039,637 B2 | 8/2018 | Maimon |
| 10,039,642 B2 | 8/2018 | Hillukka |
| 10,098,735 B2 | 10/2018 | Lei |
| 10,098,763 B2 | 10/2018 | Lei |
| 10,117,742 B2 | 11/2018 | Braido |
| 10,143,551 B2 | 12/2018 | Braido |
| 10,182,907 B2 | 1/2019 | Lapeyre |
| 10,195,023 B2 | 2/2019 | Wrobel |
| 10,226,340 B2 | 3/2019 | Keren |
| 10,231,834 B2 | 3/2019 | Keidar |
| 10,238,490 B2 | 3/2019 | Gifford, III |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,376,363 B2 | 8/2019 | Quadri |
| 10,383,725 B2 | 8/2019 | Chambers |
| 10,390,943 B2 | 8/2019 | Hernandez |
| 10,405,974 B2 | 9/2019 | Hayes |
| 10,433,961 B2 | 10/2019 | Mclean |
| 10,470,880 B2 | 11/2019 | Braido |
| 10,492,907 B2 | 12/2019 | Duffy |
| 10,500,041 B2 | 12/2019 | Valdez |
| 10,507,107 B2 | 12/2019 | Nathe |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,524,910 B2 | 1/2020 | Hammer |
| 10,531,951 B2 | 1/2020 | Spargias |
| 10,537,427 B2 | 1/2020 | Zeng |
| 10,555,809 B2 | 2/2020 | Hastings |
| 10,555,812 B2 | 2/2020 | Duffy |
| 10,561,495 B2 | 2/2020 | Chambers |
| 10,595,992 B2 | 3/2020 | Chambers |
| 10,610,362 B2 | 4/2020 | Quadri |
| 10,667,905 B2 | 6/2020 | Ekvall |
| 10,667,909 B2 | 6/2020 | Richter |
| 10,702,379 B2 | 7/2020 | Garde |
| 10,702,380 B2 | 7/2020 | Morriss |
| 10,709,560 B2 | 7/2020 | Kofidis |
| 10,751,169 B2 | 8/2020 | Chambers |
| 10,751,170 B2 | 8/2020 | Richter |
| 10,751,172 B2 | 8/2020 | Para |
| 10,758,265 B2 | 9/2020 | Siegel |
| 10,779,935 B2 | 9/2020 | Scorsin |
| 10,779,936 B2 | 9/2020 | Pollak |
| 10,779,968 B2 | 9/2020 | Giasolli |
| 10,786,351 B2 | 9/2020 | Christianson |
| 10,828,152 B2 | 11/2020 | Chambers |
| 10,856,983 B2 | 12/2020 | Keränen |
| 10,869,756 B2 | 12/2020 | Al-Jilaihawi |
| 10,874,513 B2 | 12/2020 | Chambers |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,007,054 B2 | 5/2021 | Braido |
| 11,013,599 B2 | 5/2021 | Subramanian |
| 11,026,782 B2 | 6/2021 | Chambers |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,096,781 B2 | 8/2021 | Gurovich |
| 11,147,666 B2 | 10/2021 | Braido |
| 11,154,239 B2 | 10/2021 | Toth |
| 11,154,396 B2 | 10/2021 | Dibie |

(56) References Cited

U.S. PATENT DOCUMENTS

| | | |
|---|---|---|
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |
| 11,278,406 B2 | 3/2022 | Straubinger |
| 11,351,028 B2 | 6/2022 | Peterson |
| 11,389,293 B2 | 7/2022 | Torrianni |
| 11,395,734 B2 | 7/2022 | Lee |
| 11,413,141 B2 | 8/2022 | Morin |
| 11,419,716 B2 | 8/2022 | Braido |
| 11,452,628 B2 | 9/2022 | Diedering |
| 11,458,013 B2 | 10/2022 | Righini |
| 2001/0005787 A1 | 6/2001 | Oz |
| 2002/0161377 A1 | 10/2002 | Rabkin |
| 2002/0072710 A1 | 12/2002 | Stewart et al. |
| 2003/0057156 A1 | 3/2003 | Peterson |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0137622 A1 | 6/2005 | Griffin |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado, III |
| 2006/0276874 A1 | 12/2006 | Wilson |
| 2007/0016288 A1 | 1/2007 | Gurskis |
| 2007/0156233 A1 | 7/2007 | Kapadia et al. |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0234814 A1 | 9/2008 | Salahieh et al. |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |
| 2009/0125096 A1 | 5/2009 | Chu |
| 2009/0143852 A1 | 6/2009 | Chambers |
| 2009/0171447 A1 | 7/2009 | Von Segesser |
| 2009/0171456 A1 | 7/2009 | Kveen |
| 2009/0198315 A1 | 8/2009 | Boudjemline |
| 2009/0248134 A1 | 10/2009 | Dierking |
| 2009/0248143 A1 | 10/2009 | Laham |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1* | 8/2010 | Watson ............ A61M 25/0147 604/95.04 |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0217382 A1 | 8/2010 | Chau et al. |
| 2010/0256749 A1 | 10/2010 | Tran |
| 2010/0262157 A1 | 10/2010 | Silver |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0137397 A1* | 6/2011 | Chau ................. A61F 2/2409 623/2.37 |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0269051 A1 | 11/2011 | Wijenberg |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1* | 5/2012 | Asleson ............. A61F 2/2427 606/129 |
| 2012/0197193 A1 | 8/2012 | Krolik et al. |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0090728 A1 | 4/2013 | Solem |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0226286 A1 | 8/2013 | Hargreaves |
| 2013/0231736 A1 | 9/2013 | Essinger |
| 2013/0238089 A1 | 9/2013 | Lichtenstein et al. |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |

(56) References Cited

U.S. PATENT DOCUMENTS

| | | |
|---|---|---|
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |
| 2014/0088696 A1 | 3/2014 | Figulla |
| 2014/0114340 A1 | 4/2014 | Zhou |
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0142691 A1 | 5/2014 | Pouletty |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramani |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson et al. |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0358224 A1 | 12/2014 | Tegels |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088248 A1 | 3/2015 | Scorsin |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | McNamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Mdlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |

(56) References Cited

U.S. PATENT DOCUMENTS

| | | |
|---|---|---|
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | Mccann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0136412 A1 | 5/2016 | Mckinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramani |
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0242905 A1 | 8/2016 | Chambers |
| 2016/0250022 A1 | 9/2016 | Braido |
| 2016/0250051 A1 | 9/2016 | Lim |
| 2016/0256168 A1 | 9/2016 | Nielsen |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0331529 A1 | 11/2016 | Marchand |
| 2016/0346081 A1 | 12/2016 | Zeng |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079781 A1 | 3/2017 | Lim |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0095256 A1 | 4/2017 | Lindgren |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1 | 6/2017 | Kuetting |
| 2017/0202525 A1 | 7/2017 | Piazza |
| 2017/0252191 A1 | 9/2017 | Pacetti |
| 2017/0281193 A1 | 10/2017 | Asirvatham |
| 2017/0348098 A1 | 12/2017 | Rowe |
| 2017/0360570 A1 | 12/2017 | Berndt et al. |
| 2018/0014830 A1 | 1/2018 | Neumann |
| 2018/0055629 A1 | 3/2018 | Oba et al. |
| 2018/0092744 A1 | 4/2018 | Von Oepen |
| 2018/0116843 A1 | 5/2018 | Schreck |
| 2018/0116848 A1 | 5/2018 | Mchugo |
| 2018/0133012 A1 | 5/2018 | Nathe |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0333102 A1 | 11/2018 | De Haan et al. |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0151067 A1 | 5/2019 | Zucker |
| 2019/0201192 A1 | 7/2019 | Kruse |
| 2019/0247189 A1 | 8/2019 | Dale |
| 2019/0365534 A1 | 12/2019 | Kramer |
| 2019/0365538 A1 | 12/2019 | Chambers |
| 2020/0000592 A1 | 1/2020 | Lee |
| 2020/0030088 A1 | 1/2020 | Vidlund |
| 2020/0069423 A1 | 3/2020 | Peterson |
| 2020/0069449 A1 | 3/2020 | Diedering |
| 2020/0100897 A1 | 4/2020 | Mclean |
| 2020/0113682 A1 | 4/2020 | Chang |
| 2020/0113719 A1 | 4/2020 | Desrosiers et al. |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |

(56) References Cited

U.S. PATENT DOCUMENTS

| | | | |
|---|---|---|---|
| 2020/0188101 | A1 | 6/2020 | Chambers |
| 2020/0222179 | A1 | 7/2020 | Chambers |
| 2020/0253733 | A1 | 8/2020 | Subramanian |
| 2020/0261219 | A1 | 8/2020 | Kumar |
| 2020/0276013 | A1 | 9/2020 | Chambers |
| 2020/0315678 | A1 | 10/2020 | Mazzio et al. |
| 2020/0337765 | A1 | 10/2020 | Smith |
| 2020/0368023 | A1 | 11/2020 | Kheradvar |
| 2020/0375733 | A1 | 12/2020 | Diedering |
| 2021/0236274 | A1 | 8/2021 | Benson |
| 2021/0236276 | A1 | 8/2021 | Diedering |
| 2021/0275297 | A1 | 9/2021 | Berndt |
| 2021/0275301 | A1 | 9/2021 | Kumar |
| 2021/0290383 | A1 | 9/2021 | Chambers |
| 2022/0031451 | A1 | 2/2022 | Spence |
| 2022/0338979 | A1 | 10/2022 | Benichou |
| 2023/0218397 | A1 | 7/2023 | Chambers et al. |

FOREIGN PATENT DOCUMENTS

| | | | |
|---|---|---|---|
| AU | 2013201970 | B2 | 3/2016 |
| CN | 2820130 | Y | 9/2006 |
| CN | 100413471 | C | 8/2008 |
| CN | 100444811 | C | 12/2008 |
| CN | 101953723 | A | 1/2011 |
| CN | 101953724 | A | 1/2011 |
| CN | 101953725 | A | 1/2011 |
| CN | 101953728 | A | 1/2011 |
| CN | 101953729 | A | 1/2011 |
| CN | 101961269 | A | 2/2011 |
| CN | 101961273 | A | 2/2011 |
| CN | 102036622 | | 4/2011 |
| CN | 201870772 | U | 6/2011 |
| CN | 203290964 | U | 11/2013 |
| CN | 103431931 | A | 12/2013 |
| CN | 203379235 | U | 1/2014 |
| CN | 103598939 | A | 2/2014 |
| CN | 103610520 | A | 3/2014 |
| CN | 203619728 | U | 6/2014 |
| CN | 203677318 | U | 7/2014 |
| CN | 104287804 | A | 1/2015 |
| CN | 104352261 | A | 2/2015 |
| CN | 204133530 | U | 2/2015 |
| CN | 204181679 | U | 3/2015 |
| CN | 204246182 | U | 4/2015 |
| CN | 204318826 | U | 5/2015 |
| CN | 104688292 | A | 6/2015 |
| CN | 102985033 | B | 8/2015 |
| CN | 204581598 | U | 8/2015 |
| CN | 204581599 | U | 8/2015 |
| CN | 204683686 | U | 10/2015 |
| CN | 105596052 | A | 5/2016 |
| CN | 105615936 | A | 6/2016 |
| CN | 205286438 | U | 6/2016 |
| CN | 108348270 | | 7/2018 |
| CN | 107252363 | B | 4/2020 |
| CN | 106913909 | B | 9/2020 |
| CN | 107007887 | B | 10/2020 |
| DE | 102010021345 | A1 | 11/2011 |
| EP | 2596754 | A1 | 5/2013 |
| EP | 2967858 | A2 | 1/2016 |
| EP | 2982336 | A1 | 2/2016 |
| EP | 2967845 | B1 | 8/2018 |
| EP | 2950752 | B1 | 7/2022 |
| JP | 2016531722 | A | 10/2016 |
| WO | WO1995016476 | A1 | 6/1995 |
| WO | WO2009127973 | A2 | 10/2009 |
| WO | WO2014210299 | A1 | 12/2014 |
| WO | WO2015004173 | A1 | 1/2015 |
| WO | WO2016100806 | A1 | 6/2016 |
| WO | WO2019006387 | | 1/2019 |

OTHER PUBLICATIONS

International Preliminary Report on Patentability, dated Aug. 1, 2019 in PCT Application No. PCT/US18/14400, filed Jan. 19, 2018.
Australian Examination Report in Application No. 2019280018, Jan. 14, 2021.
Canadian Office Action in Application No. 3,050,113, Apr. 1, 2020.
Chinese Office Action in Application No. 201880007705.2, Apr. 25, 2021.
European Office Action in Application No. 18741447.9, Apr. 29, 2021.
Indian Office Action in Application No. 201917028147, Dec. 29, 2021.
Japanese Office Action in Application No. 2019-538492, Jun. 29, 2022.
International Search Report and Written Opinion in Application No. PCT/US2018/14400, May 15, 2018.
European Office Action in Application No. 18741447.9, Sep. 20, 2023.
Office Action in Indian Application No. 201917028147, Feb. 14, 2024.

* cited by examiner

SYSTEMS, METHODS AND DEVICES FOR DELIVERY SYSTEMS, METHODS AND DEVICES FOR IMPLANTING PROSTHETIC HEART VALVES

CROSS-REFERENCE TO RELATED APPLICATIONS

This application is a continuation of U.S. patent application Ser. No. 15/874,376, filed Jan. 18, 2018 and entitled SYSTEMS, METHODS AND DEVICES FOR DELIVERY SYSTEMS, METHODS AND DEVICES FOR IMPLANTING PROSTHETIC HEART VALVES and also claims the benefit of U.S. Provisional Ser. No. 62/448,036, filed Jan. 19, 2017 and entitled SYSTEMS, METHODS AND DEVICES FOR DELIVERY SYSTEMS, METHODS AND DEVICES FOR IMPLANTING PROSTHETIC HEART VALVES, the entirety of which are hereby incorporated by reference.

STATEMENT REGARDING FEDERALLY SPONSORED RESEARCH OR DEVELOPMENT

Not Applicable

INCORPORATION BY REFERENCE

All references, including but not limited to publications, patent applications and patents mentioned in this specification are hereby incorporated by reference to the same extent and with the same effect as if each reference was specifically and individually indicated to be incorporated by reference.

FIELD OF THE INVENTION

The inventions described herein relate to delivery systems, devices and methods for delivering and/or positioning a cardiac valve.

BACKGROUND OF THE INVENTION

The human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of.

Native heart valves may be, or become, dysfunctional for a variety of reasons and/or conditions including but not limited to disease, trauma, congenital malformations, and aging. These types of conditions may cause the valve structure to either fail to properly open (stenotic failure) and/or fail to close properly (regurgitant).

Mitral valve regurgitation is a specific problem resulting from a dysfunctional mitral valve. Mitral regurgitation results from the mitral valve allowing at least some retrograde blood flow back into the left atrium from the right atrium. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

Native heart valves generally, e.g., mitral valves, therefore, may require functional repair and/or assistance, including a partial or complete replacement. Such intervention may take several forms including open heart surgery and open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access routes: transapical; transfemoral; transatrial; and transseptal delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

However, known delivery systems, devices and methods still suffer from significant flaws in delivery methodology including, inter alia, positioning and recapture capability and efficiency.

In addition, known "replacement" heart valves are intended for full replacement of the native heart valve.

Therefore, these replacement heart valves physically engage the annular throat and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as a supplementary functional valve as well as be fully capable of replacing the native function of a valve that has lost most or all of its functionality. However, the inventive solutions described infra will apply generally to all types and forms of heart valve devices, unless otherwise specified.

Finally, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the annular through) connected from the stent device down through the annular throat, with the sub-annular surface within the left ventricle, the left ventricular chordae tendineae and even into the left ventricle wall surface(s).

Such 2-chamber solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the annulus, annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, the inventive solutions described herein are readily applicable to single or 2-chamber solutions, unless otherwise indicated.

Various embodiments of the several inventions disclosed herein address these, inter alia, issues.

DETAILED DESCRIPTION OF THE INVENTION

Various embodiments of the present invention are disclosed in the Figures for providing percutaneous access to the valve of interest via one of at least the following known access routes: transapical; transfemoral; transatrial; and transseptal delivery techniques. Each of these access routes may be used for the embodiments disclosed herein.

Figure 1:
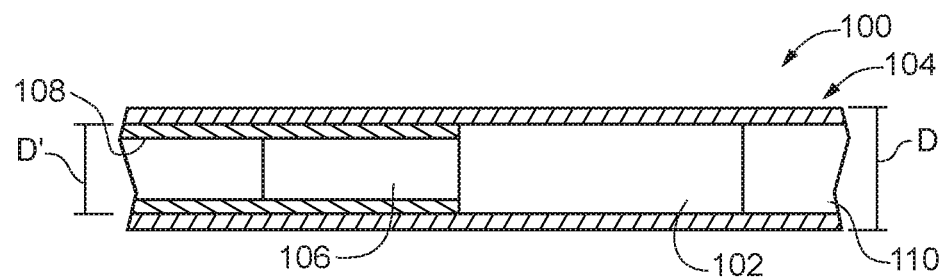
FIG. 1 illustrates a side cutaway view of one embodiment of the present invention.

Thus, FIG. 1 illustrates one embodiment of a prosthetic valve device 100 with a 2-part frame in collapsed configuration. The distal portion 102 of the collapsed device comprises the valve with prosthetic leaflets with a portion of the supporting frame, and is longitudinally translatably and rotatably confined within the lumen of an outer sheath 104 having a first outer diameter D. The proximal portion 106 of the collapsed device 100 comprises the remaining supporting frame which is in operative connection with the distal portion 102 of collapsed device 100 and in longitudinally translatably and rotatably confined within the lumen of an inner sheath 108 that is at least longitudinally translatable relative to the outer sheath 104 and wherein the outer sheath 104 is at least longitudinally translatable relative to the inner sheath 108. The inner and/or outer sheath 108, 104 may also be rotationally translatable relative to the other sheath. The inner sheath 108 is disposed within the lumen of the outer sheath 104 and, therefore, the inner sheath 108 comprises a second outer diameter D' that is smaller than the outer sheath's outer diameter D.

The preferred configuration of the device of FIG. 1 comprises the collapsed device 100 consisting of one unit with a proximal and distal portion 106,102 as shown. The outer sheath 104 may be retracted to release expose firstly the distal portion 102 from the distal end 110 of the outer sheath 104 for initial expansion and positioning in the subject chamber of the heart. Alternatively, the distal portion 102 of the device 100 may be pushed distally to be released from the distal end 110 of the outer sheath 104 in response to distal translation of the inner sheath 108, e.g., or to a push rod pushing against the proximal portion 106 of the device 100. In the case of a push rod, the proximal portion 106 will eventually be pushed distally out of the smaller lumen of the inner sheath 106 and into the larger lumen of the outer sheath 104 where an interim secondary expansion of the proximal portion 106 occurs, followed by the secondary positioning expansion when the proximal portion 106 is eventually released from the distal end 110 of the outer sheath 104.

If expanded within the left atrium in connection with a prosthetic mitral valve, the lower portion of the distal portion 102 may be positioned against the upper surface of the annulus within the left atrium.

In this configuration, if the distal portion 102 is properly positioned and released/expanded, then the secondary release and expansion of the proximal portion 106 of the device 100 may be initiated and achieved according to the alternative methods described above in connection with the initial release and expansion of the distal portion 102. The skilled artisan will recognize that once the initial positioning expansion of the distal portion 102 is accomplished, then the secondary positioning expansion of the proximal portion 106 will also be properly located and positioned.

The configuration of FIG. 1, in its various embodiments, enables delivery of a device 100 comprising a frame that may be slightly oversized for the chamber, e.g., atrial, dimensions through the two-step frame positioning expansion method. Some frames in collapsed form may be as much as 2x in longitudinal length than any chamber, e.g., atrial, dimension. Thus, the staged positioning expansion method is necessary for delivery.

Figure 2A:
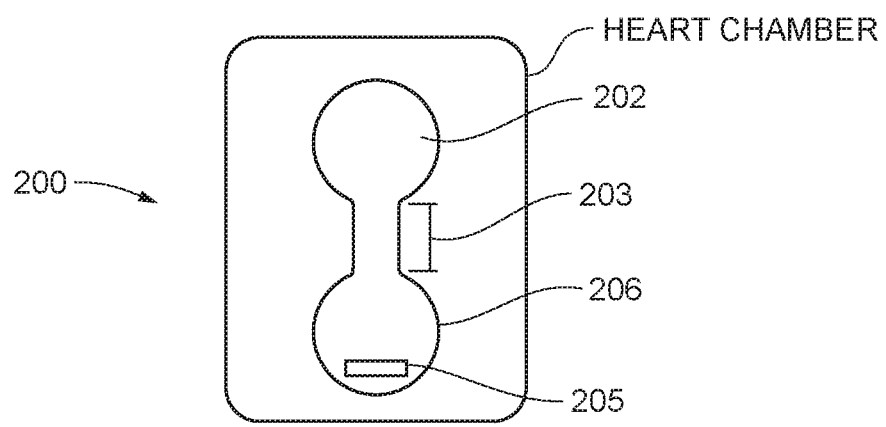
FIG. 2A illustrates a side view of one embodiment of the present invention.
Figure 2B:
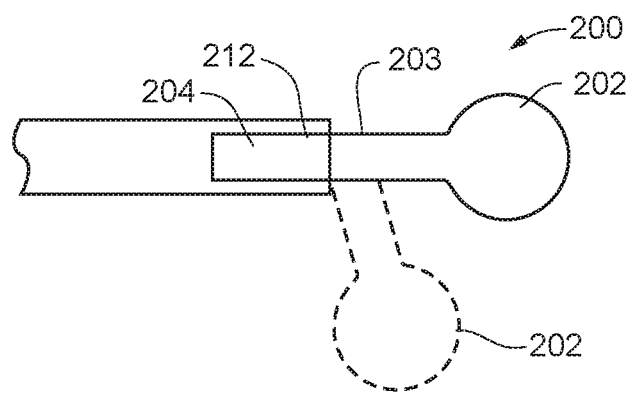
FIG. 2B illustrates a side cutaway view of one embodiment of the present invention.

Turning now to FIGS. 2A and 2B a prosthetic valve device 200 comprising a supporting stent frame, with prosthetic valve attached and/or supported therein, is provided wherein the design comprises two portions (distal 202 and proximal 206, wherein the prosthetic valve with leaflets 205 is held/supported within the distal portion 202) with expanded diameters that are connected by a central portion 203 that has a smaller diameter than the expanded diameters of the two portions 202, 206. As illustrated, the two portions 202, 206 comprise an undeformed and fully expanded spherical shape, though other shapes may be used as the skilled artisan will readily understand. Certain embodiments may comprise at least one of the proximal and distal portions 206, 202 having an expanded sizing that is slightly larger than the subject chamber's dimensions, e.g., the left atrial dimensions to allow expansion anchoring. Moreover, the aspect ratio of each of the two portions 206, 202 may vary.

As shown, the collapsed stent with valve is held within the lumen of a delivery sheath 204, with a distal portion that holds or supports the device 200 therein being released from the end 210 of the delivery sheath 204 with subsequent positioning expansion of same within the subject chamber, e.g., the left atrium. When proper positioning is confirmed, the remaining central portion 203 (if not previously released along with the distal portion 202) and/or the proximal portion 206 may then be released and positionally expanded by methods described in connection with FIG. 1, including use of an inner sheath as described above and/or a push rod to translate the device 200 out of the distal end 210 of the outer delivery sheath 204. As with FIG. 1, this embodiment comprises a two-step or staged delivery mechanism. Both FIG. 1 and FIG. 2A/2B sets of embodiments may comprise a coating or covering on the distal portion 202 while the proximal portion 206 may comprise an open frame formed from, e.g., stent cells. In the case of FIG. 2A/2B, the central portion 202 may also comprise and open cell construction and uncovered. The dashed lines of FIG. 2B show an alternate embodiment wherein the expanded delivered portion 202 comprises a hinge point 212 to assist in orienting the prosthetic valve and leaflets within distal portion 202 downward toward the native valve.

Figure 3A:
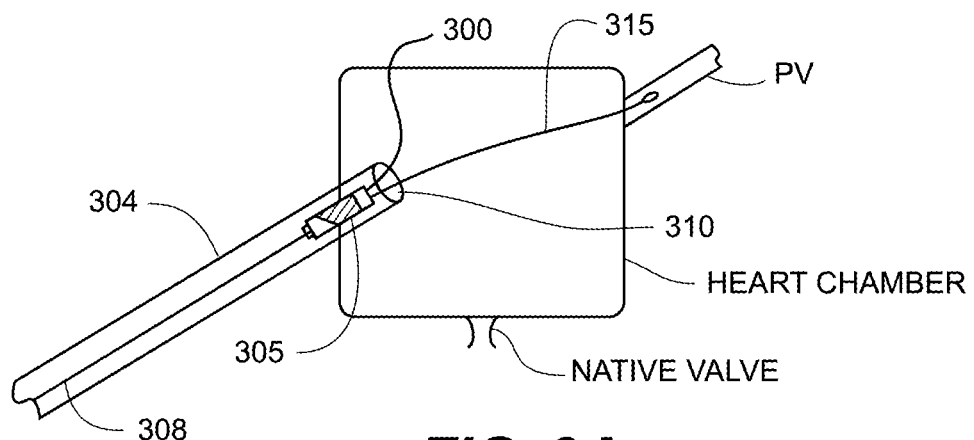
FIG. 3A illustrates a side cutaway view of one embodiment of the present invention.
Figure 3B:
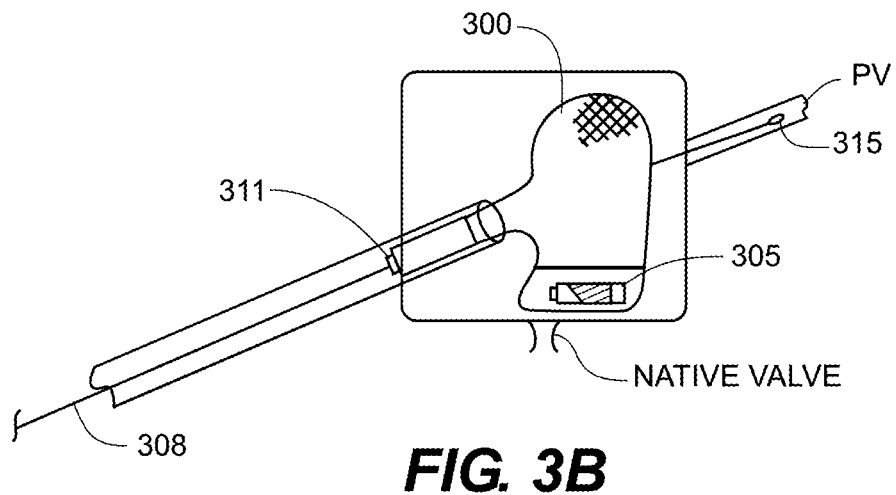
FIG. 3B illustrates a side cutaway view of one embodiment of the present invention.

FIGS. 3A, 3B, 3C, 5A and 5B provide further disclosure of exemplary prosthetic valve devices with support means, e.g., stented and associated exemplary delivery methods. Thus FIG. 3A shows the collapsed device 300 in the lumen of a delivery sheath 304 in operative communication with a push/pull rod 308 actuated by the device operator that is capable of distally translating the collapsed device 300 as in FIG. 3A out of the distal end 310 of the delivery sheath 304 for positioning expansion and, conversely, pulling the expanded device 300 as shown in FIG. 3B back into the distal end 310 of the delivery sheath 304 if necessary. The push/pull rod 308 may also allow in certain embodiments the rotation of the collapsed device 300 within the lumen of the delivery sheath 310 to aid in positioning prior to release and expansion. Further, the operative communication of the push/pull rod 308 with the collapsed device 300 may comprise a screw or clip release mechanism 311 connected with the most proximal portion of the collapsed device 300. The base or lower portion of the device 300 may be covered with tissue or other biocompatible material while the upper portion of the device may comprise an open cell construction.

Generally, the collapsed device 300 is loaded and positioned within the delivery sheath 304 with the valve portion 305 oriented in a downward position as shown. This allows the collapsed valve device 305 to be pushed out of the delivery sheath 304 in a sideways orientation as illustrated and enables the expanding valve device 300 upon release from the delivery sheath to be properly oriented to the native valve and subject chamber, e.g., mitral valve and left atrium.

In certain cases, an alignment wire 315 may be translated from the delivery sheath 304 into a pulmonary vein, e.g., the left upper pulmonary vein PV to assist in positioning and delivery of the device 300.

Figure 4:
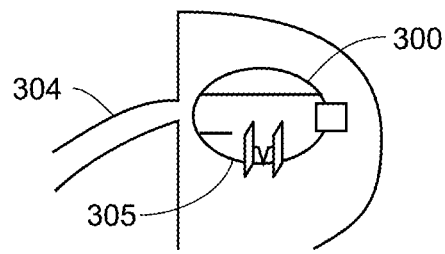
FIG. 4 illustrates a side cutaway view of one embodiment of the present invention.

FIG. 4 illustrates a sideways delivery of device 300 during expansion and just after delivery from the outer end 310 of the delivery sheath 304, wherein the delivered device is oriented substantially vertically and aligned for positioning over the native valve.

Figure 5A:
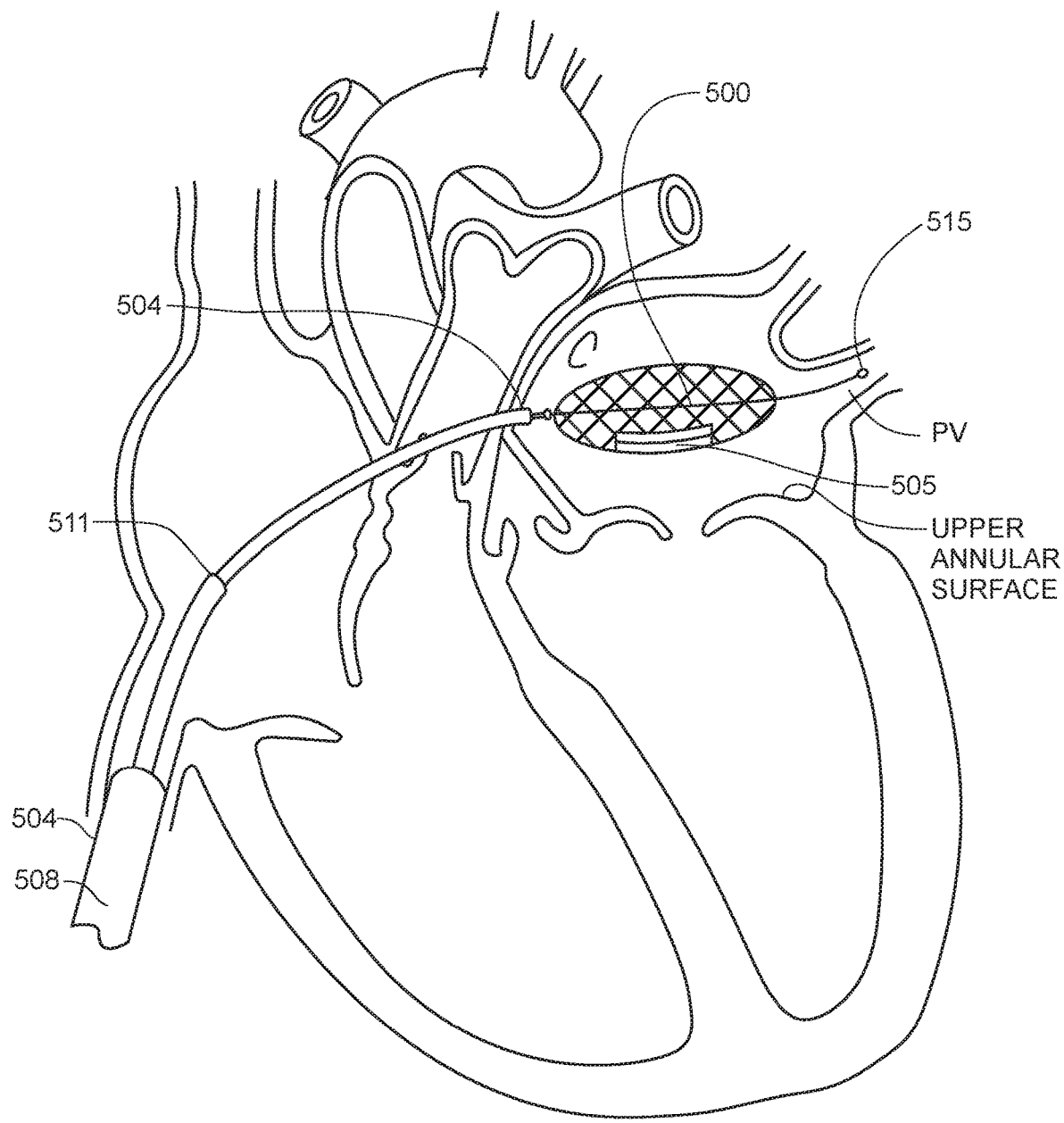
FIG. 5A illustrates a side cutaway view of one embodiment of the present invention.
Figure 5B:
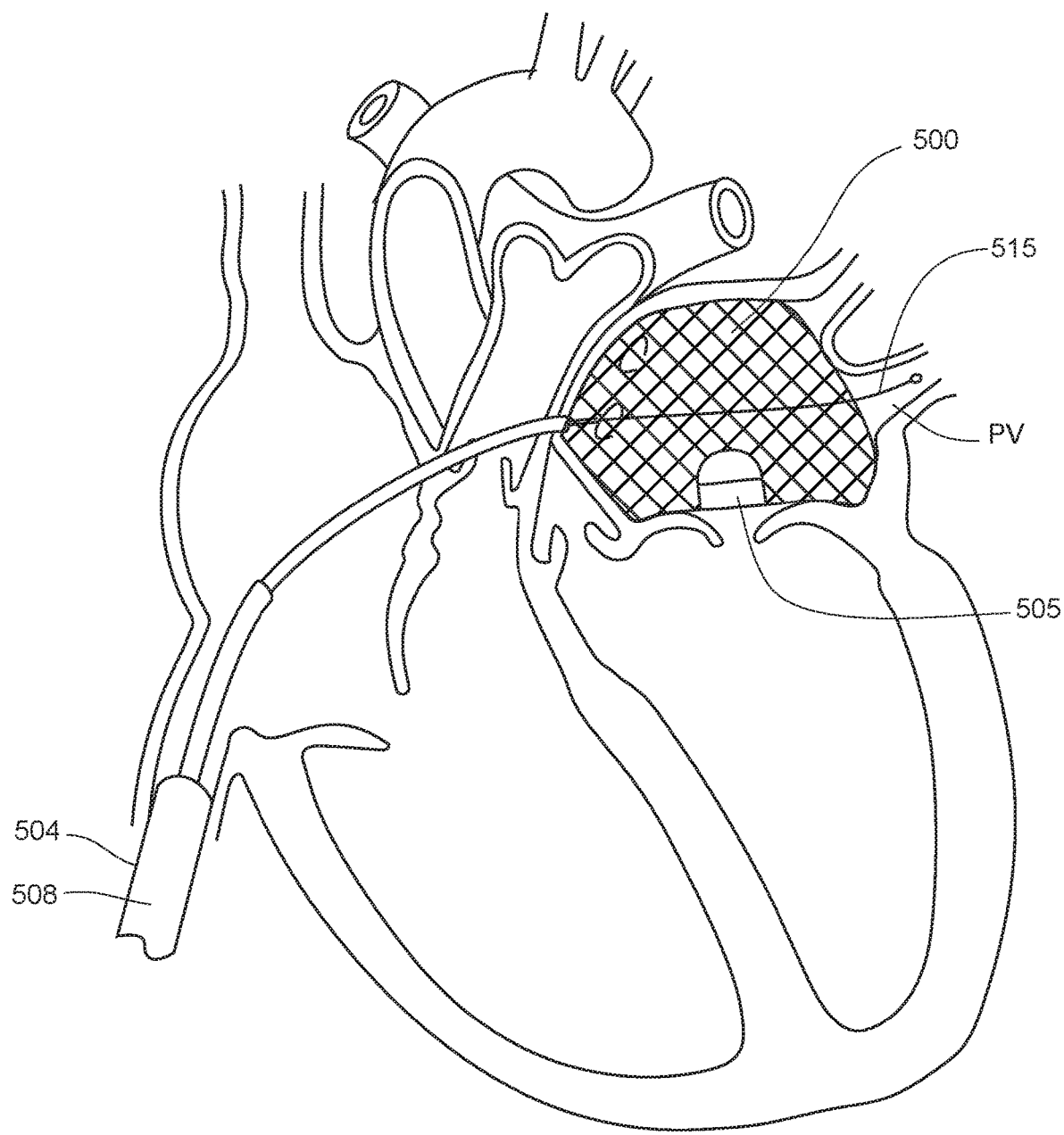
FIG. 5B illustrates a side cutaway view of one embodiment of the present invention.

Thus, as shown best in FIGS. 5A and 5B, the prosthetic valve device 500 may be delivered sideways (with the valve portion 505 oriented on the bottom as shown), asymmetrically and may comprise a locating element 515 in operative connection with the prosthetic valve device 500 and that extends from the delivery sheath 503 with at least a distal end of the locating element 515 or push tube disposed within a pulmonary vein PV, e.g., the left upper pulmonary vein as shown. This system provides a self-centering system that may expand upon releasing/translating the collapsed prosthetic valve device 500 from the distal end 510 of the delivery sheath 504. As shown a push tube 508 and associated connector 511 may be used to assist in manipulating the orientation of the prosthetic valve device 500 once it is delivered from the distal end 510 of the delivery sheath 504.

Figure 6A:
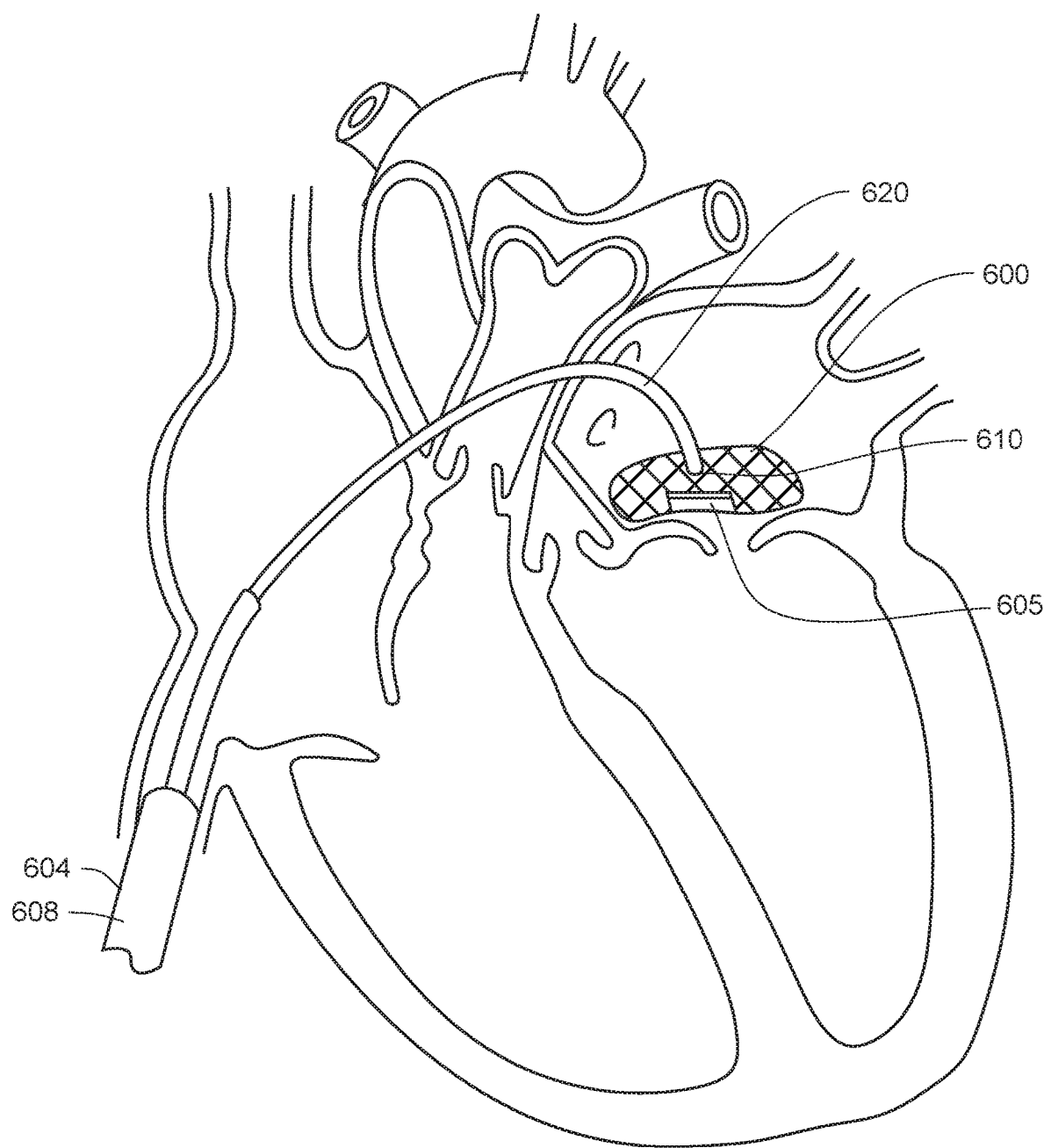
FIG. 6A illustrates a side cutaway view of one embodiment of the present invention.
Figure 6B:
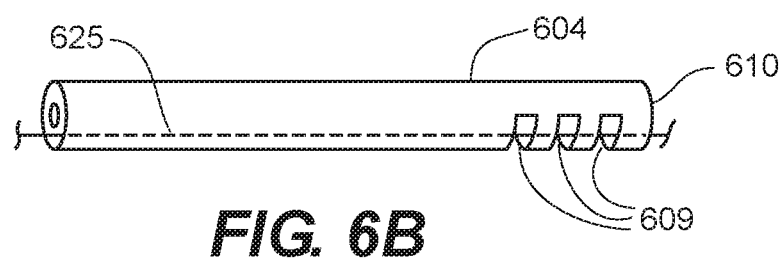
FIG. 6B illustrates a side cutaway view of one embodiment of the present invention.
Figure 6C:
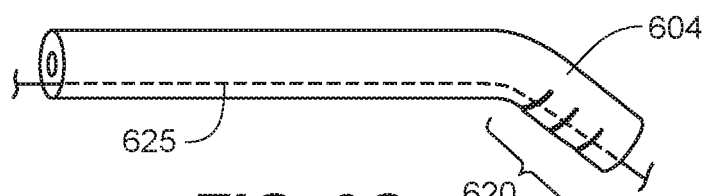
FIG. 6C illustrates a side cutaway view of one embodiment of the present invention.

Turning now to FIGS. 6A-6C, the prosthetic valve device 600 is delivered using a delivery catheter or sheath 604 comprises either a pre-curved distal portion 620 or a distal portion adapted to be able to be curved 620 to present a substantially straight distal section within the atrium. FIG. 6A provides a pre-curved embodiment, curved to enable loading of a prosthetic valve device 600 in a configuration that places the valved bottom portion 605 in the proper location on release from the distal end 610 of the pre-curved distal portion 620 of the delivery catheter or sheath, more specifically from the straightened distal section distal to the pre-curved distal portion 620. Thus, as shown, the valve supported portion 605 of the collapsed and expandable frame/stent is distal-most within the lumen of the delivery catheter/sheath 604. The pre-curved portion 620 enables easy orienting of the valved portion 605 with an exemplary mitral valve and/or upper surface of the annulus thereof.

Thus, the delivery system with a curved distal portion as in FIG. 6A enables the prosthetic valve device 600 to be positioned over the annulus and native valve leaflets. When positioned over the annulus and native valve leaflets, the curved delivery catheter or sheath 604 may be withdrawn proximally, alone or in combination with a push rod 608 or similar device on the proximal side of the prosthetic valve device 600, to release and deliver the prosthetic valve device 600 into the left atrium and expand the delivered device 600. It is noteworthy that the curved delivery catheter or sheath 604 comprises in some embodiments a straight distal end within the left atrium and located distal to the curved section 620 wherein the compressed prosthetic valve device 600 is translated and manipulated around the curved portion 620 of the curved delivery catheter or sheath 604. The compressed prosthetic valve device 600 may be assisted in translating around the curved portion 620 of the curved delivery catheter or sheath by including a suture attachment to the distal end of the implant, a pull wire attached to the distal end of the implant extending to the proximal end of the delivery catheter or sheath, or by taking advantage of the natural flexion point in the arrangement of FIG. 1 between the proximal and the distal portions of the prosthetic valve device and/or by a hinging point as in FIG. 2.

FIGS. 6B and 6C comprise an alternative approach to creating the curved portion 620 by enabling curving of the distal portion of the delivery sheath or catheter 604 by providing a series of cuts or serrations 609 along a bottom portion surface of the sheath or catheter, resulting in a weak region susceptible to bending. As shown a pull wire 625 is attached to the distal end 610 of the catheter 604 along this bottom weak cut or serrated region and is disposed through the catheter/sheath lumen to an operator who may pull the wire with force F proximally to achieve the desired curvature prior to release of the collapsed prosthetic valve structure 600 which is oriented in collapsed form as in FIG. 6A and released for positioning expansion virtually directly on the subject valve or upper annular surface. The cuts 609 may extend through the catheter/sheath wall completely or may only be sections that have a catheter/sheath wall that is thinner than the rest of the catheter/sheath walls. The cuts 609 shown are uniform and generally square, though any depth, shape and uniform or non-uniform spacing of same may be used to achieve the weakened region.

Figure 7A:
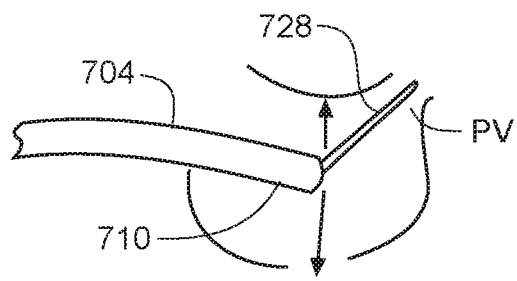
FIG. 7A illustrates a side cutaway view of one embodiment of the present invention.
Figure 7B:
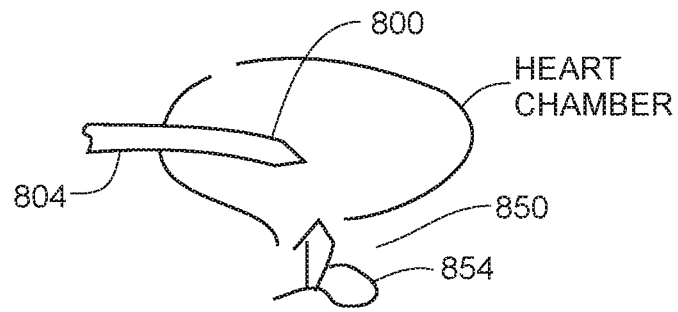
FIG. 7B illustrates a side cutaway view of one embodiment of the present invention.

FIGS. 7A and 7B illustrate delivery systems for an exemplary prosthetic valve, e.g., mitral valve replacement or supplement, to a heart chamber, e.g., the left atrium using a delivery catheter or sheath 704 as shown in FIG. 7A with transseptal access and in combination with an additional guidance tool 728 used to help guide the expanding valved device (not shown) as it is released from the distal end 710 of the catheter or sheath 704 using methods or devices described herein. The additional guidance tool 728 may be disposed within the upper pulmonary vein PV, for example. The guidance tool 728 may be hingedly or rotatingly attached to the catheter or sheath 704 enabling the tool 728 to rotate into position. A pull wire similar to that shown in FIGS. 6B and 6C may be used to connect to and manipulate the tool 728 into position.

FIG. 7B illustrates two delivery systems, a first delivery system 800 for alignment and deployment and a second delivery system 850 for recapture and repositioning if needed. One of the delivery systems, either the first 800 or the second 850, may access the subject heart chamber via a transfemoral access method while the other delivery system may access the subject heart chamber via another transvenous access method. The first delivery system 800 may thus comprise a delivery catheter or sheath 804 as described elsewhere herein while the second delivery system may comprise a recapture and repositioning catheter or sheath 854, similar in structure to the delivery catheter/sheath 804.

Figure 8A:
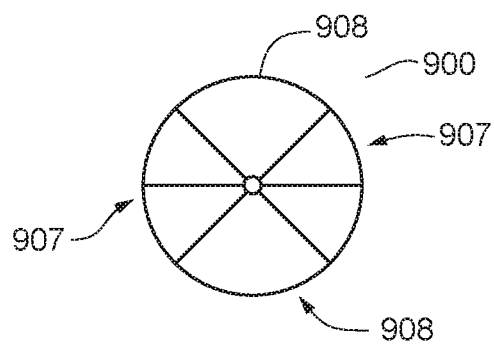
FIG. 8A illustrates a top view of one embodiment of the present invention.
Figure 8B:
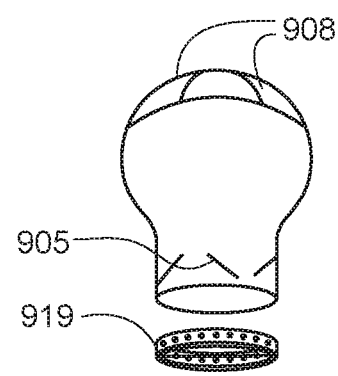
FIG. 8B illustrates a side and partially exploded view of one embodiment of the present invention.

FIGS. 8A and 8B illustrate embodiments designed to facilitate accurate positioning of a prosthetic heart valve within a chamber, e.g., the left atrium, including but not limited to self-centering and fluoroscopy techniques. In this embodiment of a prosthetic stented valve device 900, with the prosthetic valve and leaflets 905 supported proximate the bottom portion of the valve device, the upper portion 909 of the device 900 may be divided into subsections as shown from the top in FIG. 8A. The illustrated case provides 4 subsections, though other numbers of subsections may certainly be useful and are within the scope of the present invention. As shown, opposing subsections are either open cell or open wire construction 907 or are comprised of a fabric in the form of a type of sail 908. Upon delivery of this device 900 to a subject heart chamber, the fabric sails 908 will catch and use the natural force of blood flow to maneuver the device frame 900 into proper positioning with subsequent release and expansion when positioning is confirmed.

FIG. 8B is a related concept, but also includes an annulus spacer 919 that may be delivered first via a delivery catheter/sheath as described previously herein and in certain embodiments, the spacer may be directed into position with a guidewire positioned within the lumen of the delivery catheter/sheath and further moved out of the distal end of the delivery catheter/sheath and either proximate to (on the proximal side) of the chamber upper annular surface or may be disposed at least partway within the annular throat. Once released from the lumen and distal end of the delivery catheter/sheath, the annular spacer 919 may expand from a delivered collapsed form and positioned on the upper annular surface which may space the prosthetic valve and leaflets 905 from the upper annular surface. Subsequently, the prosthetic valve device, as described herein and which may, or may not, comprise sails 908 as in FIG. 7A, is delivered from the delivery catheter/sheath and positionally expanded to connect with the previously positioned spacer 919.

Figure 9A:
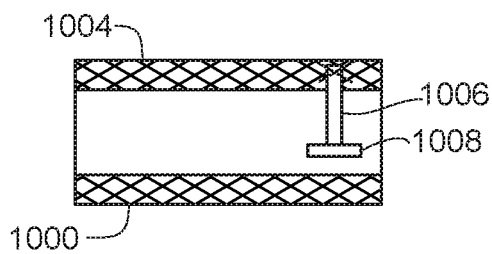
FIG. 9A illustrates a side cutaway view of one embodiment of the present invention.

We next describe positional orienting delivery structures in FIGS. 9A-9D. Generally, each of these prosthetic valved devices are designed for use in the left atrium and make use of the left atrial appendage (LAA) as an orienting mechanism. FIG. 9A therefore comprises an LAA plug 1006 disposed on a side surface of the collapsed device 100 within the delivery sheath 1004 lumen and, in FIG. 9B, the LAA plug 1006 is positioned at least partially within the LAA. Once the LAA is engaged by the LAA plug 1006, the operator has confirmation that the valved prosthetic device 1000 is in correct position. This device may be used in combination with any of the previously described devices and methods, including but not limited to the staged 2-step delivery devices and methods, whereby an initial positioning expansion would result in orienting the LAA plug into the LAA, then the secondary positioning expansion of the rest of the device initiated by release from the distal end of a delivery sheath.

Figure 9B:
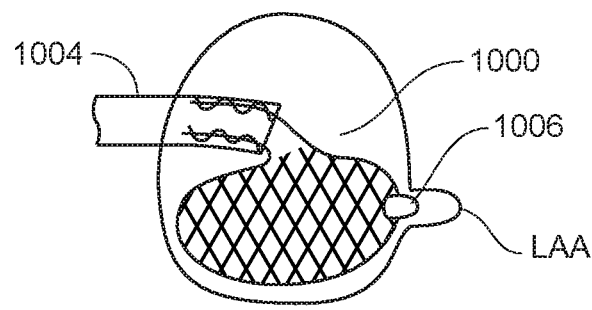
FIG. 9B illustrates a side cutaway view of one embodiment of the present invention.

An additional benefit of certain embodiments of FIGS. 9A and 9B may be to employ the LAA plug 1006 as a device to prevent clotting within the LAA, wherein the LAA plug 1006 fills the LAA entirely and/or an outer flange 1008 covers the LAA opening entirely to prevent any blood clots from forming and/or moving out of the heart to potentially cause a stroke.

Figure 9C:
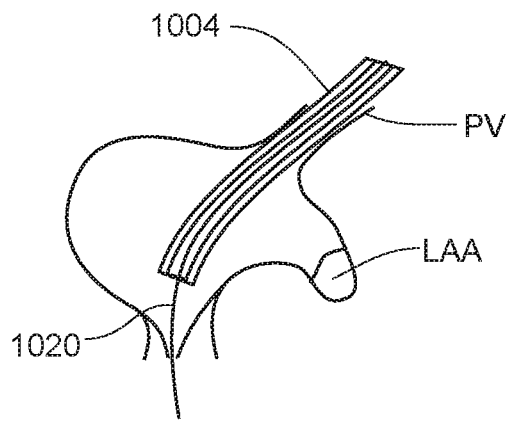
FIG. 9C illustrates a side cutaway view of one embodiment of the present invention.
Figure 9D:
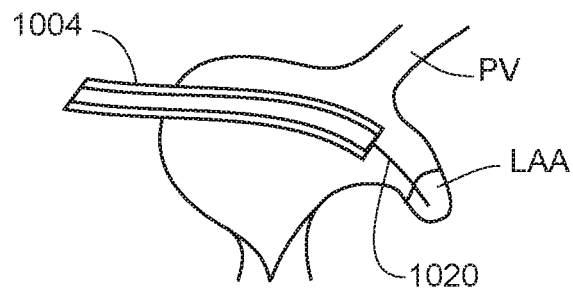
FIG. 9D illustrates a side cutaway view of one embodiment of the present invention.

FIG. 9D shows a slightly different mechanism whereby a guidewire 1020 is disposed through a delivery sheath 1004 and into the LAA to provide orienting guidance for the positioning expansion (1 step or staged) of the collapsed prosthetic valved device (not shown) within the lumen of delivery sheath 1004. The sheath 1004 may be pulled back to deploy/release the valved device (not shown) from the distal end of the sheath 1004 for positioning expansion or a push rod may be used to push the valved device out of the sheath's distal end as previously described. In these cases, the guidewire 1020 positioned within the LAA provides a key orienting guidance parameter so that the operator knows positioning will be proper on expansion. The guidewire 1020 may comprise an atraumatic tip to prevent damaging the tissue of the LAA.

FIG. 9C illustrates another alignment/orienting system wherein the delivery catheter/sheath 1004 is introduced via a pulmonary vein PV, e.g., the upper pulmonary vein, into the left atrium and a guidewire 1020 disposed through the lumen of the delivery catheter/sheath 1004 and into, or proximate, the annulus, i.e., the annular throat, as a guide for the to-be-delivered valved device (not shown but compressed and self-expanding as previously described). When the sheath 1004 is pulled back, or a push rod is used to push the collapsed valved device out of the distal end of the delivery catheter or sheath 1004, the expanding valved device may slide down over the pre-positioned guidewire 1020 to a proper position when fully expanded.

Figure 10A:
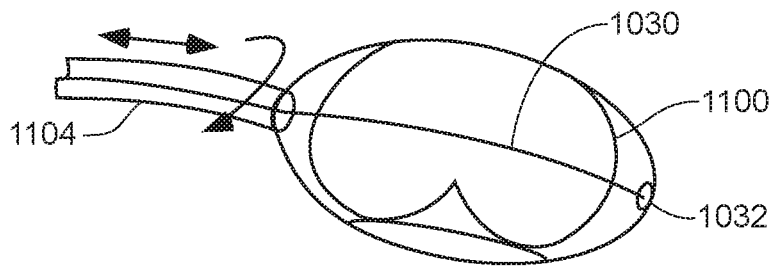
FIG. 10A illustrates a side cutaway view of one embodiment of the present invention.
Figure 10B:
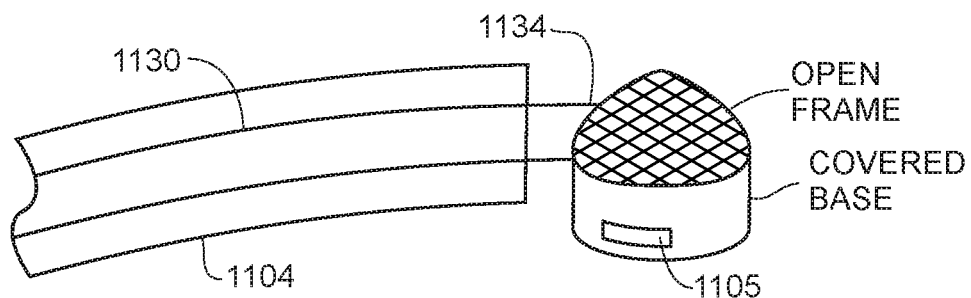
FIG. 10B illustrates a side cutaway view of one embodiment of the present invention.

FIG. 10A illustrates a partially expanded stented valved device 1100 released from the delivery catheter sheath. At least one capture wire 1030 (shown radially wrapped around the device 1100, but may take other wrapping positions) is shown and which restrains the expandable device 1100 from fully expanding until properly positioned within the subject heart chamber, e.g., the left atrium. When proper position is confirmed, the capture wire 1030 may be removed by cutting and withdrawal distally through the delivery sheath 1004 lumen or by disconnecting a connector pin or latch 1032 or equivalent to enable full expansion of the device 1100 at the proper positional location. FIG. 10B is similar with an alignment wire 1130 that assists in positional orientation as it feeds out of the distal end of the delivery catheter/sheath 1104 while in connection with the partially expanding sheath at 2 or 3 or more stabilization points 1034 until proper position is confirmed. The stabilization point 1134 connections may hold the partially expanded device in that state until proper position is confirmed, then the connections may be removed, either by cutting (as in the case of a releasable suture) or by disconnecting a connector pin or latch, to enable the full expansion at the proper positional location or by provision of a secondary over the wire cutter introduced via the delivery catheter/sheath 1104 to clip alignment wire 1130.

Figure 10C:
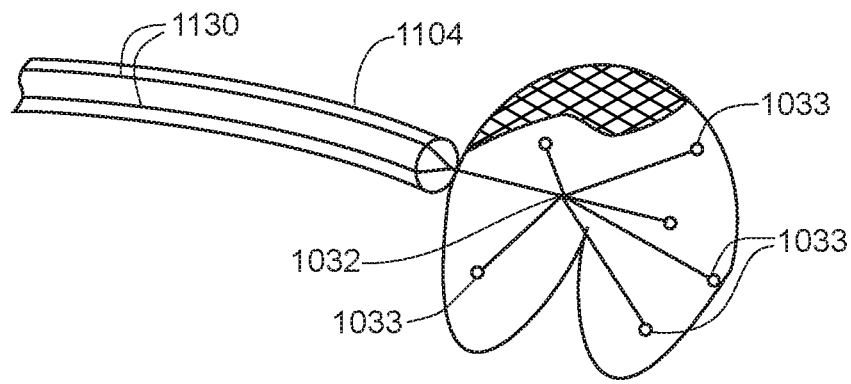
FIG. 10C illustrates a side cutaway view of one embodiment of the present invention.

FIG. 10C provides an alternative prosthetic heart valve device shown in a positionally expanded position after release from the distal end of the delivery catheter/sheath 1104 and comprising at least one attachment point 1032 located within the stented heart valve device as well as two or more pull/push wires 1130 with a first end connected to the at least one attachment point 1032 and a second end attached to points 1033 around the stent frame. This arrangement may function in several different ways to facilitate recapture, repositioning and/or redeployment.

First, one embodiment may comprise the two or more pull/push wires 1130 of a length that is slightly smaller than the chamber, e.g., left atriam, dimensions to ensure proper positioning. Once position is confirmed as proper, the pull/push wires 1130 may be released by, e.g., a secondary over the wire cutter or other means to disengage the pull/push wire connection between the at least one attachment point 1032 and the two or more pull/push wires 1130, thereby enabling the full expansion of the properly positioned frame within the chamber. As with other embodiments described herein, the fully expanded frame may be slightly larger than at least one dimension to facilitate anchoring.

Another embodiment may further comprise a push rod disposed translationally within the delivery catheter/sheath 1104 lumen and that also provides a distally extending releasable connector attached to the at least one attachment point 1032 within the stented heart valve frame for disengaging the attachment between the at least one attachment point 1032 and the two or more push/pull wires 1130 once proper positioning is confirmed. This embodiment provides the further benefit of using a distally extending releasable connector tool to pull proximally on the at least one attachment point wherein the attachment point and the push/pull wires are connected to points on the stent frame that, when proximal force is applied to the attachment point, cause the stent frame to collapse slightly or fully, to enable repositioning. Once repositioned, distal force is applied to the releasable connector tool to fully expand the prosthetic valve frame.

Yet another embodiment may comprise the attachment point 1132, push/pull wires 1130, and/or the connection of the push/pull wires to the stent frame to be formed of a material that dissolves over a short time period.

Figure 11:
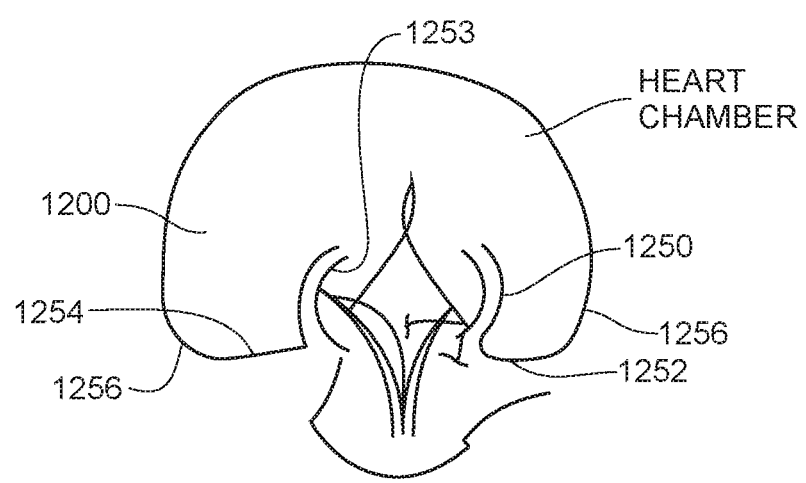
FIG. 11 illustrates a side cutaway view of one embodiment of the present invention.

FIG. 11 illustrates a prosthetic valve device 1200 comprising a ball and socket relationship between the support frame (socket or partial socket), with the prosthetic valve and leaflets 1253 disposed therein (ball or partial ball). In this embodiment, the outer frame 1250 is, as illustrated, a partial sphere having a radiusing and a central point 1252, with the central point 1252 disposed generally around the native valve and annulus. The outer frame 1250 may comprise a radially extending flange 1254 to connect and seal with the upper annular surface and may further comprise wall elements 1256 extending upward from at least portions of the radially extending flange 1252 to connect with and seal against the chamber, e.g., left atrial, walls. The radially extending flange 1252 may comprise an expandable stent-like construction to provide radial expansive force to assist in anchoring the device 1200. Alternative constructions may comprise any of the prosthetic stented valve frames described herein, e.g. and without limitation, an upper open expandable frame with a lower expandable frame covered with tissue.

The prosthetic valve further comprises an inner partial sphere 1253 with a radiusing that matches, or is complementary with, the radiusing of the outer frame's partial sphere 1250, but with a smaller radius that the outer frame 1250 as the inner partial sphere 1253 resides within the outer frame's partial sphere 1250. The prosthetic leaflets are supported within the inner partial sphere 1253. The inner partial sphere 1253 may comprise a friction fit with the outer frame's partial sphere 1250 so that some movement is possible in all dimensions, including rotational, without losing the proper valve position relative to the native valve and/or annulus. Alternatives may allow a looser friction fit so that the inner partial sphere essentially floats within the outer frame's partial sphere, thereby allowing a fuller range of motion than a tighter friction fit.

Figure 12:
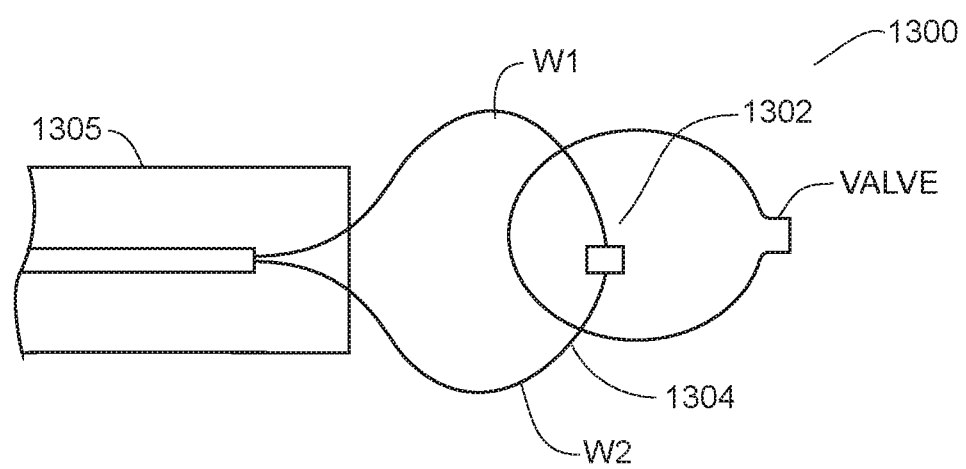
FIG. 12 illustrates a side view of one embodiment of the present invention.

FIG. 12 illustrates an implant frame with prosthetic valve device 1300 attached thereto connected via a connector element 1302 to a lasso structure 1304 that is, in turn, operatively connected with a manipulation wire 1306, that may comprise a single wire or two wires, that extends proximally to the operator who is then able to manipulate the lasso 1304 and connector element 1302. The lasso structure 1304 may comprise two distal wires, W1, W2, or more than two distal wires, in operative connection with the connector element 1302. If the manipulation wire 1306 comprises two wires W1, W2, then a first of the two wires may be connected with wire 1 and the second of the two wires may be connected with wire 1. Wires W1, W2 may be disconnected from the connector element 1302 by the operator's pulling of one, or both, of the manipulation wire(s) W1, W2. The lasso structure 1304 may, as shown, be expandable to a diameter that is larger than the inner diameter of the catheter's 1305 lumen and is disposed through the implant frame structure with the connector element 1302 in operative connection with the lasso 1304 and the device frame 1300 generally in the middle of the implant structure. This configuration allows the operator to steer the device 1300 with the lasso structure 1304 during deployment and also allows retrieval back into the catheter's 1305 lumen if necessary. The connector element 1302 may be configured together with the device's 1300 frame structure to enable collapsing of the device's 1300 frame structure to allow pullback of the device's 1300 structure into the catheter's 1305 lumen. The connector element 1302 may also be disconnected by the operator from the device's 1300 frame, whereby one, or both, of the wires W1, W2 are disconnected and the lasso structure 1304 retracted proximally through the catheter 1305. In other embodiments, the connector element 1302 may remain attached to the device's 1300 frame structure when the operator disconnects wires W1, W2 from the connector element 1302 and pulls the lasso structure 1304 proximally through the catheter sheath 1305.

The description of the various inventions, embodiments thereof and applications as set forth herein is illustrative and is not intended to limit the scope of the invention. Features of various embodiments may be combined with other embodiments within the contemplation of these inventions. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the inventions.

What is claimed is:

1. A method of delivering a self-expanding prosthetic mitral valve device comprising prosthetic mitral valve leaflets to an implantation site within a left atrium of a patient's heart, comprising:
   accessing the left atrium with a delivery catheter having a proximal end, a distal end and a lumen therethrough;
   loading the self-expanding prosthetic mitral valve device in a collapsed configuration into the lumen of the delivery catheter at the proximal end thereof, wherein the collapsed configuration of the prosthetic mitral valve device comprises a prosthetic mitral valve attached thereto;
   delivering the collapsed prosthetic mitral valve device out of the distal end of the delivery catheter and into the left atrium at a location proximate the implantation site;
   allowing the delivered self-expanding prosthetic mitral valve device to expand within the left atrium at the implantation site, wherein at least a portion of the expanded prosthetic mitral valve device engages at least a portion of an upper annular surface within the left atrium without engaging a left ventricle of the patient's heart;
   wherein the collapsed self-expanding prosthetic mitral valve device further comprises a proximal portion and a distal portion, wherein the prosthetic mitral valve leaflets are disposed within the distal portion;
   loading an inner sheath into the delivery catheter lumen, the inner sheath having a distal end that engages the collapsed self-expanding prosthetic mitral valve device, wherein translation of the inner sheath through the delivery catheter lumen results in translation of the collapsed self-expanding prosthetic mitral valve device, which includes a one-chamber stented valve, through the delivery catheter lumen; and
   wherein the inner sheath comprises a lumen therethrough sized to receive the proximal portion of the collapsed self-expanding prosthetic mitral valve device.

2. The method of claim 1, wherein the distal end of the inner sheath engages the distal portion of the collapsed self-expanding prosthetic mitral valve device, wherein the distal portion is not received within the lumen of the inner sheath.

3. The method of claim 1, wherein the distal portion is delivered, positioned proximate the implantation site and expanded before the proximal portion of the collapsed self-expanding prosthetic mitral valve device is delivered and expanded.

4. The method of claim 1, further comprising:
   providing a plug attached to a side of the distal portion of the collapsed self-expanding prosthetic mitral valve device; aligning the plug with a left atrial appendage of the patient's heart; and
   engaging the left atrial appendage with the plug when the self-expanding mitral valve device is expanded.

5. The method of claim 4, wherein the plug further comprises a flange that engages and seals the atrial wall around the left atrial appendage.

6. The method of claim 1, further comprising:
   providing a push rod that is connected to the collapsed prosthetic mitral valve device; and
   pushing the collapsed prosthetic mitral valve device with the push rod through the lumen of the delivery catheter for delivery and expansion within the left atrium.

7. The method of claim 6, further comprising at least partially collapsing the expanded prosthetic mitral valve device within the lumen of the delivery catheter by pulling proximally on the push rod.

8. The method of claim 6, further comprising: translating a locating element through the lumen of the delivery catheter; engaging an open frame portion of the prosthetic mitral valve device with the locating element; and engaging the lumen of a left upper pulmonary vein of the patient's heart with a distal end of the locating element before delivering the prosthetic mitral valve device into the left atrium.

9. The method of claim 8, wherein the locating element extends through an open frame section of the prosthetic mitral valve device.

10. The method of claim 1, further comprising providing a central portion disposed between the proximal portion and the distal portion, the central portion having a maximum diameter that is smaller than a maximum diameter of the proximal portion and a maximum diameter of the distal portion.

11. The method of claim 10, further comprising:
providing a hinge on the central portion;
delivering the central portion out of the distal end of the delivery catheter lumen to expose the hinge to the left atrium; and
rotating the distal portion toward the upper annular surface of the left atrium; and delivering the proximal portion out of the distal end of the delivery catheter lumen and into the left atrium.

12. The method of claim 1, further comprising:
translating an alignment wire disposed through the lumen of the delivery catheter;
engaging an open frame portion of the prosthetic mitral valve device with the alignment wire; and
engaging a left upper pulmonary vein of the patient's heart with the alignment wire before delivering the prosthetic mitral valve device into the left atrium along the alignment wire.

13. The method of claim 1, further comprising at least one capture wire extending through the delivery catheter lumen and engaging the self-expanding prosthetic mitral valve device adapted to restrain the expansion of the prosthetic mitral valve device to a partially expanded configuration.

14. The method of claim 13, further comprising the at least one capture wire further adapted to positionally orient the partially expanded prosthetic mitral valve device by manipulating the at least one capture wire at the proximal end of the delivery catheter.

15. The method of claim 14, further comprising:
positionally orienting the partially expanded prosthetic mitral valve device within the left atrium;
confirming proper orientation of the partially expanded prosthetic mitral valve device;
removing the at least one capture wire; and
allowing the partially expanded prosthetic mitral valve device to fully expand.

16. The method of claim 15, further comprising providing a push/pull rod through the lumen of the delivery catheter adapted to assist in positionally orienting the partially expanded prosthetic mitral valve device.

17. The method of claim 1, further comprising a lasso element attached to the prosthetic mitral valve device adapted to be manipulated at the proximal end of the delivery catheter; manipulating the lasso element to positionally orient, prevent full expansion of the prosthetic mitral valve device and/or allow full expansion of the prosthetic mitral valve device within the left atrium.

18. The method of claim 1, wherein the self-expanding prosthetic mitral valve device further comprises an upper portion formed from a stent comprising at least two sets of opposing subsections, at least one set of the opposing subsections comprising a fabric covering.

19. The method of claim 18, further comprising using the fabric covering to capture blood flow to position the self-expanding prosthetic mitral valve device and expanding the positioned self-expanding prosthetic mitral valve device.

20. The method of claim 1, further comprising ensuring that the left ventricle is not touched at any point by the expanded prosthetic mitral valve device.

21. The method of claim 1, wherein the left atrium is accessed through a septum between the right atrium and left atrium of the patient's heart.

22. The method of claim 1, further comprising: translating an alignment wire through the lumen of the delivery catheter and engaging an open frame portion of the prosthetic mitral valve device; and engaging the lumen of a left upper pulmonary vein of the patient's heart with a distal end of the alignment wire before delivering the prosthetic mitral valve device into the left atrium along the alignment wire.

23. The method of claim 1, further comprising an alignment guide wire disposed through the lumen of the delivery catheter and engaging a left atrial appendage of the patient's heart.

24. The method of claim 1, wherein the delivery catheter comprises a pre-curved distal portion adapted to facilitate positioning of the self-expanding prosthetic mitral valve device within the left atrium.

25. The method of claim 1, further comprising:
providing a pull wire that is attached to the distal end of the delivery catheter and extends proximally out of the proximal end of the delivery catheter;
providing a weakened section around at least a portion of a distal portion of the delivery catheter and proximate to the attachment of the pull wire to the distal end of the delivery catheter; and
curving the distal end of the delivery catheter by pulling the pull wire proximally during at least the delivery of the prosthetic mitral valve device.

* * * * *